United States Patent [19]

Foster et al.

[11] Patent Number: 5,294,597
[45] Date of Patent: Mar. 15, 1994

[54] HERBICIDAL CARBOXAMIDE DERIVATIVES

[75] Inventors: Christopher J. Foster, Faversham; Terence Gilkerson, Canterbury; Richard Stocker, Rochester, all of England

[73] Assignee: Shell Research Limited, United Kingdom

[21] Appl. No.: 663,722

[22] Filed: Mar. 4, 1991

[30] Foreign Application Priority Data

Mar. 16, 1990 [GB] United Kingdom ............... 90059650

[51] Int. Cl.$^5$ .................... A01N 43/40; C07D 213/64
[52] U.S. Cl. ........................ 504/255; 546/298
[58] Field of Search ............ 546/298; 71/94; 504/255

[56] References Cited

U.S. PATENT DOCUMENTS 4,270,946  6/1981  Gutman ................... 71/94
4,327,218  4/1982  Gutman ................... 71/94

FOREIGN PATENT DOCUMENTS 63-17811  1/1988  Japan .
2087887  6/1982  United Kingdom .

OTHER PUBLICATIONS

Michaely et al., Chapter 5 of "Synthesis and Chemistry of Agrochemicals", 1987, published by the American Chem. Soc., pp. 55-64.

Primary Examiner—Jane T. Fan

[57] ABSTRACT

Compounds of formula

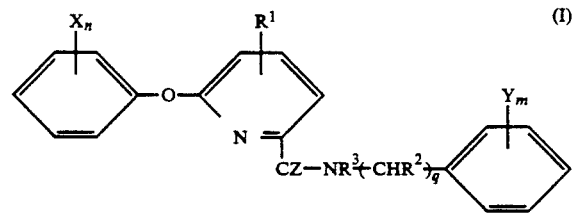

wherein
- Z is oxygen or sulphur;
- $R^1$ is hydrogen, halogen, alkyl or haloalkyl;
- $R^2$ is hydrogen, or alkyl;
- q is 0 or 1;
- $R^3$ is hydrogen, alkyl or alkenyl; the or each X independently is halogen, optionally substituted alkyl or alkoxy, alkenyloxy, alkynyloxy, cyano, carboxy, alkoxycarbonyl, (alkylthio)carbonyl, alkylcarbonyl, amido, alkylamido, nitro, alkylthio, haloalkylthio, alkenylthio, alkynylthio, alkylsulphinyl, alkylsulphonyl, alkyloximinoalkyl or alkenyloximinoalkyl;
- n is 0 or an integer from 1 to 5; the or each Y independently is a halogen, alkyl, nitro, cyano, haloalkyl, alkoxy or haloalkoxy; and m is 0 or an integer from 1 to 5, their preparation and use as herbicides.

12 Claims, No Drawings

HERBICIDAL CARBOXAMIDE DERIVATIVES

This invention relates to certain new herbicidal carboxamide derivatives, their preparation, herbicidal compositions containing such derivatives and their use in combating undesired plant growth.

More specifically, the invention concerns novel N-phenyl phenoxypyridine carboxamide compounds.

The herbicidal activity of N-phenyl-2-phenoxy-3-pyridine carboxamide compounds is known, for example from U.S. Pat. Nos. 4,270,946 and 4,327,218, and from U.K. Patent Specification No. 2 087 887. One example in the U.K. Patent Specification No. 2 087 887 is the commercial compound N-(2,4-difluorophenyl)-2-(3-trifluoromethylphenoxy)-3-pyridine carboxamide (diflufenican).

This class of compounds, and diflufenican in particular, is discussed in detail in Pesticide Science 1987, 18, 15–28. In terms of the herbicidal utility of the compounds, emphasis is placed, in the Pesticide Science reference, upon their effectiveness in controlling broad-leaved weeds in winter cereals. The class of compounds is also described in "Synthesis and Chemistry of Agrochemicals", chapter 5, published by Am. Chem. Soc., (1987).

Certain N-phenyl-4-phenoxy-3-pyridine carboxamide compounds, and N-oxides thereof, are generally covered in Japanese Patent Application No. J6 3017-811A, for use with other active ingredients in herbicidal compositions. However in the examples only compounds having 4-phenoxy and 4-(3-chlorophenoxy) substituents are specifically disclosed (Compounds A31, A32 and A33).

There is no indication in the prior art references of any herbicidal activity in other structural isomers.

We have investigated other structural isomers of N-phenyl phenoxypyridine carboxamide compounds, and have found uniformly low or limited herbicidal activity in the following classes:
N-phenyl-2-phenoxy-4-pyridinecarboxamides,
N-phenyl-2-phenoxy-5-pyridinecarboxamides,
N-phenyl-3-phenoxy-5-pyridinecarboxamides,
N-phenyl-4-phenoxy-2-pyridinecarboxamides,
N-phenyl-3-phenoxy-2-pyridinecarboxamides,
N-phenyl-3-phenoxy-4-pyridinecarboxamides,
N-phenyl-3-phenoxy-6-pyridinecarboxamides.

However, we have surprisingly found excellent herbicidal activity in one particular class of compounds, N-phenyl-2-phenoxy-6-pyridinecarboxamides. Indeed comparison between the prior art commercial compound diflufenican and the closest compound in this new class of herbicidal compounds, the correspondingly substituted 2,6-isomer, shows a greater herbicidal activity against important representative grass species, Echinochloa crusgalli, and broadleaf species, Beta vulgaris, with an equally low action against the cereal species, Zea mays, for the 2,6-compound. A number of other compounds in this new group of herbicidas exhibit yet greater activity than diflufenican against such representative grass and broadleaf species.

Accordingly, the present invention provides a compound of the general formula I

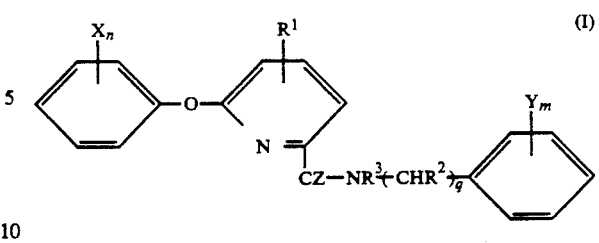

in which
Z represents an oxygen or sulphur atom;
$R^1$ represents a hydrogen or halogen atom or an alkyl or haloalkyl group;
$R^2$ represents a hydrogen atom or an alkyl group;
q represents 0 or 1;
$R^3$ represents a hydrogen atom or an alkyl or alkenyl group;
the or each group X independently represents a halogen atom or an optionally substituted alkyl or alkoxy group, or an alkenyloxy, alkynyloxy, cyano, carboxy, alkoxycarbonyl, (alkylthio)carbonyl, alkylcarbonyl, amido, alkylamido, nitro, alkylthio, haloalkylthio, alkenylthio, alkynylthio, alkylsulphinyl, alkylsulphonyl, alkyloximinoalkyl or alkenyloximinoalkyl group; n is 0 or represents an integer from 1 to 5; the or each group Y independently represents a halogen atom or an alkyl, nitro, cyano, haloalkyl, alkoxy or haloalkoxy group; and m is 0 or represents an integer from 1 to 5.

In general terms, unless otherwise stated herein, the term alkyl as used herein in respect of a radical or moiety refers to a straight or branched chain radical or moiety. Suitably an alkyl moiety has from 1 to 6 carbon atoms, preferably from 1 to 4 carbon atoms. A preferred alkyl moiety is an ethyl or, especially, a methyl group and a preferred alkoxy moiety is ethoxy or, especially, methoxy.

Unless otherwise stated in this specification when an alkyl or alkoxy group is designated as being optionally substituted, the substituent groups which are optionally present may be any of those customarily employed in the development of biocidal compounds, and/or the modification of such compounds to influence their structure/activity, persistence, penetration or other property. Specific examples of such substituents include halogen, especially fluorine, chlorine or bromine atoms, and phenyl, cyano, amino, hydroxy, alkoxy and (alkyl)amino groups, alkyl groups suitably having 1 or 2 carbon atoms. Preferred substituents are halogen, especially fluorine, atoms.

In general terms, unless otherwise stated, as used herein the term halogen atom may denote a bromine, iodine, chlorine or fluorine atom, and is especially a chlorine or fluorine atom.

An alkylamido group may have 1 or 2 alkyl groups, for example the group $-CON(CH_3)_2$.

Preferably Z represents an oxygen atom.

Compounds of general formula I in which $R^1$ represents a hydrogen atom have been shown to be very active in combating undesired plant growth.

Preferably $R^2$ represents a hydrogen atom or a methyl group, so that, when q is 1, $-(CHR^2)_q-$ represents a methylene or ethylidene group. However, q is especially 0.

Preferably $R^3$ represents a methyl, ethyl or allyl group or a hydrogen atom. Most preferably, $R^3$ represents a hydrogen atom or a methyl group.

Suitably, the or each group X independently represents a halogen atom, especially a bromine, chlorine or fluorine atom, an alkoxy group, especially methoxy, an alkyl group, especially methyl or ethyl, a haloalkyl group, preferably a fluoroalkyl and/or a halomethyl group, especially a trifluoromethyl group, a nitro group, a carboxy group, an alkoxycarbonyl group, especially methoxycarbonyl, an alkylthiocarbonyl group, especially ethylthiocarbonyl, an amido group, an alkylamido group, especially dimethylamido, an alkylthio group, especially methylthio, an alkylsulphonyl group, especially methylsulphonyl, an alkyloximinoalkyl group, for example (1-ethoxyiminoethyl), a haloalkoxy group, preferably a fluoroalkoxy and/or a halomethoxy group, preferably a trifluoromethoxy group, an alkenyloxy group, for example allyloxy group, or a cyano group.

Preferably n is 0, or n is 1 or 2 and the or each group X independently represents a halogen atom, an alkyl group, an alkoxy group, a haloalkyl group, a haloalkoxy group, a nitro group, an alkenyloxy group, an alkylthio group, an alkylsulphonyl group, an alkyl-oximinoalkyl group or a cyano group.

When n is at least 1, one substituent X is most preferably located at the 3-position, and is a fluorine, chlorine or bromine atom or a trifluoromethyl, cyano, trifluoromethoxy or ethyl group.

Most preferably, $X_n$ represents a 3-trifluoromethyl or 3-cyano substituent.

Suitably, the or each group Y independently represents a halogen atom, especially an iodine, chlorine or fluorine atom, an alkyl group, especially methyl, a nitro or cyano group, a haloalkyl group, especially trifluoromethyl, an alkoxy group, especially methoxy, or a haloalkoxy group, especially trifluoromethoxy.

m preferably represents 0, 1, 2 or 3, most preferably 0, 1 or 2.

Preferably m is 0, or m is 1 and the group Y represents a halogen atom, or a cyano, methyl or trifluoromethyl group, or m is 2 or 3 and at least one Y is a halogen atom.

Preferably, when m is at least 1, there is a substituent Y at the 4-position.

When m is at least 2, there are suitably substituents Y at the 2- and 4-positions. When m is at least 2, the substituents Y may be different but are preferably identical.

In certain preferred compounds $Y_m$ represents 4-fluoro.

In certain preferred compounds $Y_m$ represents 2,4-difluoro.

In certain preferred compounds $Y_m$ represents 2-fluoro,5-methyl.

In certain preferred compounds $Y_m$ represents 3-fluoro.

In certain preferred compounds $Y_m$ represents. 2-fluoro.

In certain preferred compounds $Y_m$ represents 4-methyl.

In certain preferred compounds $Y_m$ represents 4-trifluoromethyl.

In certain preferred compounds $Y_m$ represents 2,4,5-trifluoro or 2,3,4-trifluoro.

In certain preferred compounds $Y_m$ represents 4-chloro.

In certain preferred compounds $Y_m$ represents 2,3-dimethyl.

In certain preferred compounds $Y_m$ represents 4-cyano.

In certain preferred compounds m is 0.

It will be appreciated that certain of the compounds of the invention, for example those in which q is 1 and $R^2$ is other than hydrogen, will exist in different stereoisomeric forms. The present invention is to be understood to include all individual stereoisomeric forms of the compounds of general formula I and mixtures thereof in whatever proportion. It will be further appreciated that one stereoisomer may have a greater activity than another stereoisomer of the same compound or than a mixture of the isomers.

The compounds of general formula I may either be prepared by reaction of an appropriate phenoxypicolinic acid derivative with an appropriate aniline or aralkylamine (method A) or by reaction of an appropriate 2-halo-6-pyridine carboxamide derivative with an appropriate alkali metal phenolate (method B). Such methods constitute further aspects of the present invention.

In accordance with method A, a compound of the general formula I wherein Z represents an oxygen atom in prepared by reacting a compound of the general formula II with a compound of the general formula III

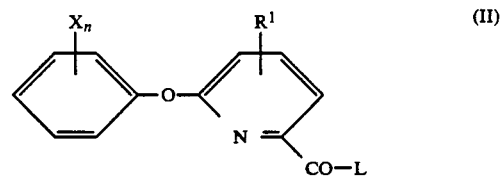

(II)

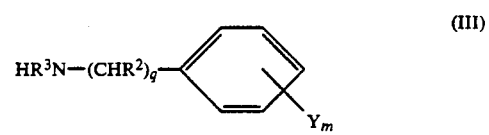

(III)

wherein $x_n$, $R^1$, $R^2$, $R^3$, q and $Y_m$ are as defined above, and L represents a leaving group.

The leaving group L may suitably be a halogen atom, for example a bromine or, especially, a chlorine atom, an alkoxy group, suitably $C_{1-4}$ alkoxy, especially methoxy, or a group of the general formula —O—CO—Q, where Q represents an alkyl group or a group of the formula

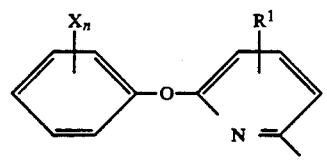

The process variant A may be carried out in the presence of an inert organic solvent, for example dimethylformamide or an aromatic hydrocarbon, for example benzene or toluene, or a halogenated hydrocarbon, for example dichloromethane or an ether, for example diethyl ether, or an ester, for example ethyl acetate; suitably at a temperature in the range 0° to 100° C. Conveniently substantially equimolar amounts of the reactants are used. It may be expedient, however, to use one reactant in excess, suitably the amine/aniline.

When L represents a halogen atom the reaction is suitably carried out at a temperature in the range 0° to 50° C., preferably at ambient temperature, and suitably in the presence of a base, for example potassium carbonate or, preferably, an amine base, such as triethylamine, or excess amine/aniline starting material.

When L represents an alkoxy group, the reaction is suitably carried out at a temperature in the range 0° to 100° C., preferably at the reflux temperature of the reaction medium, and in the absence of a base. The reaction may be carried out with or without a solvent. If a solvent is utilised, then a high boiling solvent is the most suitable type of solvent to use.

When L represents a group of the general formula —O—CO—Q a base is not required and heat may be sufficient to effect anilide formation.

Preferably L represents a chlorine atom or a methoxy group.

In accordance with method B, a compound of the general formula I wherein Z represents an oxygen atom is prepared by reacting a compound of the general formula IV with a compound of the general formula

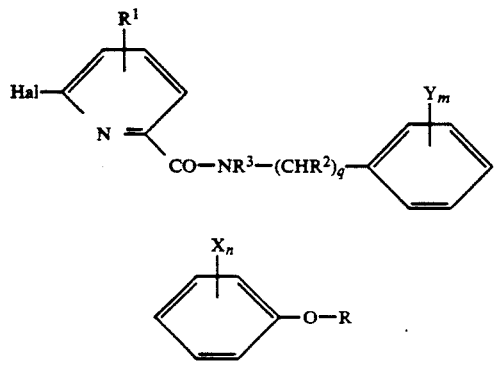

where $R^1$, $R^2$, $R^3$, q, $Y_m$ and $X_n$ are as defined above, Hal represents a halogen atom, and R represents an alkali metal atom.

Suitably, Hal represents a bromine or, especially, a chlorine atom. Suitably R represents a potassium or, especially, a sodium atom.

The reaction variant B may be carried out by preparation of the alkali metal phenolate from the phenol and an alkali metal alkoxide such as sodium methoxide, followed by treatment of the phenolate with a substantially equimolar amount of reactant IV, suitably at an elevated temperature, for example under reflux, with a copper catalyst such as cuprous chloride in pyridine in the presence of an aromatic hydrocarbon, such as xylene, as described in U.K. Patent Specification No. 2 050 168.

Alternatively the reaction B could be carried out in the presence of an alkali metal hydride, for example sodium hydride, in a dry solvent, such as dimethylformamide, suitably at an elevated temperature, for example at a temperature in the range of from 50° C. to 125° C. The reaction may alternatively be carried out in the presence of an alkali metal carbonate, for example sodium or potassium carbonate, followed by treatment with cuprous oxide and/or copper powder in an organic solvent such as dimethylformamide or quinoline. The reaction may suitably be carried out at a temperature in the range of from 20° to 150° C., conveniently at the reflux temperature.

Compounds of the general formula II may be prepared from corresponding phenoxy-substituted picolinic acids by standard methods for the preparation of, for example, esters using, for example, alcohols and acid catalysts or thionyl chloride, or of acid chlorides, bromides, anhydrides or mixed anhydrides, using, for example, thionyl chloride, thionyl bromide or acetic anhydride. The acid compounds themselves can be prepared by standard methods from chloropicolinic acid or ester thereof. Chloropicolinic acid, or ester thereof, may be prepared by the method described in J. Pharm. Belg. (1980), 35 1, 5–11.

Compounds of the general formula IV may suitably be prepared by an analogous method to that used for the reaction of compounds of the general formulae II and III by reacting an appropriately substituted aniline or amine with a 2-halo-6-pyridine carboxylic acid derivative of the general formula

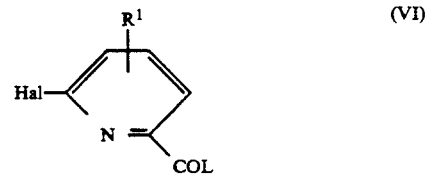

in which $R^1$, Hal and L are as defined above. Compounds of formula VI may be prepared by conventional techniques from picolinic acid.

The compounds of general formula IV are believed to be novel, and so may be considered a further aspect of the present invention, together with their preparation.

The amines/anilines of formula III and the phenolates of formula V are either known or can be prepared by conventional techniques.

Compounds of the general formula I prepared by either method A or method B above may readily be converted into other compounds of formula I by standard techniques known to those skilled in the art.

Compounds of the general formula I wherein Z represents a sulphur atom are suitably prepared by reaction of a compound of the general formula I wherein Z represents an oxygen atom, with phosphorous pentasulphide under standard conditions, for example by heating, suitably under reflux, in the presence of an inert aromatic solvent, for example benzene, toluene, pyridine or quinoline.

Compounds of the general formula I wherein a group X represents an alkyloximinoalkyl or alkenyloximinoalkyl group are suitably prepared in standard manner, for example by reaction of a corresponding compound in which X represents an alkylcarbonyl group, for example an acetyl group, with an appropriate alkyl- or alkenyl-hydroxylamine or acid addition salt thereof; suitably in the presence of an organic solvent, suitably an alcohol, for example methanol or ethanol; optionally, if a hydroxylamine salt is used, in the presence of a base, suitably an amine base such as triethylamine; and suitably at an elevated temperature, for example the reflux temperature.

The compounds of the present invention may be isolated and purified by conventional techniques, for example by solvent extraction, evaporation followed by recrystallisation or by chromatography on silica.

The compounds of the invention have been found to have surprisingly high herbicidal activity with a wide spectrum of activity against grasses and, especially, broadleaved weeds, including *Veronica persica* (speedwell), *Stellaria media* (chickweed), *Alopecurus myosur-*

*oides* (blackgrass) and *Avena fatua* (wild oat), when applied pre- and post-emergence. Examples have been found to show selectivity to small grain cereals, for example maize, wheat, barley and rice, and to broad-leaved crops, for example soya and sunflower, indicating that they may be useful in combating weeds growing in such crops.

The activity of diflufenican has been compared in tests with the compound of Example 24 of the compounds exemplified hereafter, and the latter compound appears to have certain advantages over diflufenican, for example in its activity against wild oat and blackgrass, and its selectivity in maize, sunflower and soya.

Accordingly, the invention further provides a herbicidal composition comprising a compound of formula I as defined above in association with at least one carrier, and a method of making such a composition which comprises bringing a compound of formula I into association with at least one carrier.

The invention also provides the use of such a compound or composition according to the invention as a herbicide. Further in accordance with the invention there is provided a method of combating undesired plant growth at a locus by treating the locus with a compound or composition according to the invention. Application to the locus may be pre-emergence or post-emergence. The dosage of active ingredient used, may, for example, be in the range of from 0.01 to 10 kg/ha, suitably 0.05 to 4 kg/ha. The locus may, for example, be the soil or plants in a crop area, typical crops being cereals such as wheat, barley and rice.

A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating biocidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5-10% w of active ingredient. Granules are usually prepared to have a size between 10 and 100 BS mesh (1.676-0.152 mm), and may be manufactured by agglomeration or impregnation techniques. Generally, granules will contain 0.5-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain, 10-75% w active ingredient, 0.5-15% w of dispersion agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable power or a concentrate according to the invention with water, also lie within the scope of the invention. The said emulsions may be of the water-in-oil or of the oil-in-water type, and may have a thick "mayonnaise"-like consistency.

The composition of the invention may also contain other active ingredients, for example compounds possessing insecticidal or fungicidal properties or other herbicides.

The following Examples illustrate the invention. Examples 1 to 10, 11 to 20 and 21 to 23, relate to the preparation of various classes of starting materials, and Examples 24 to 112 to the preparation of compounds of general formula I. All structures were confirmed by mass spectroscopy and 300'H nmr.

EXAMPLE 1

Preparation of methyl-6-(3-α,α,α-ti-trifluoromethylphenoxy)picolinate

A solution of sodium methoxide (from 1.3 g sodium in 20 ml methanol) was added to a solution of 3-α,α,α-trifluoromethylphenol (8.9 g) in xylene (50 ml). The solvents were evaporated in vacuo to give the dry sodium phenolate. Pyridine (25 ml) and xylene (50 ml) were added, followed by cuprous chloride (1.5 g) and the mixture heated to reflux. A solution of methyl-6-chloropicolinate (8.5 g) in xylene (50 ml) was added dropwise. The mixture was refluxed for a further 14 hours. After cooling, the mixture was poured into water (500 ml) and acidified with dilute sulphuric acid. The xylene layer was separated and the aqueous layer further extracted with diethyl ether. The combined extracts were washed with brine, dried over anhydrous magnesium sulphate and evaporated. The residue was purified on a silica gel column using 5% (v/v) diethyl ether dichloromethane as eluant to give the title compound (7.4 g) as a yellow solid of melting point 43°–44° C.

m/e Theory: Found 297:297.

| Theory for $C_{14}H_{10}O_3NF_3$: | C 56.6 | H 3.4 | N 4.7% |
|---|---|---|---|
| Found: | C 55.6 | H 3.4 | N 4.8% |

The compounds of general formula X listed in Table I below were prepared by the method of Example 1.

TABLE 1

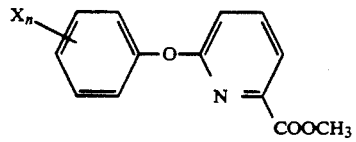

(General Formula X)

| Example No. | $X_n$ | C (Calc. Found) | H (Calc. Found) | N (Calc. Found) | Melting Point (°C.) | m/e (Theory Found) |
|---|---|---|---|---|---|---|
| 2 | — | 68.1 | 4.8 | 6.1 | 71–72 | 229 |
|   |   | 66.8 | 4.6 | 5.7 |   | 229 |
| 3 | 2,4-diCl | 52.5 | 3.0 | 4.7 | 90–91 | 297 |
|   |   | 52.8 | 3.3 | 5.0 |   | 297 |
| 4 | 3-$C_2H_5$ | 70.0 | 5.8 | 5.4 | 45–46 | 257 |
|   |   | 69.2 | 5.8 | 5.8 |   | 257 |
| 5 | 3,5-diCl | 52.5 | 3.0 | 4.7 | 108–109 | 297 |
|   |   | 51.7 | 2.7 | 4.6 |   | 297 |
| 6 | 3-O—$CH_2$—CH=$CH_2$ | 67.4 | 5.3 | 4.9 | oil | 285 |
|   |   | 65.8 | 5.2 | 5.1 |   | 285 |
| 7 | 3-$NO_2$ | 56.9 | 3.6 | 10.2 | 108–110 | 274 |
|   |   | 54.1 | 3.5 | 9.7 |   | 274 |
| 8 | 3-$OCF_3$ | 53.7 | 3.2 | 4.5 | oil | 313 |
|   |   | 55.3 | 3.6 | 4.7 |   | 313 |
| 9 | 3-Cl | 59.3 | 3.8 | 5.3 | 55–56 | 263 |
|   |   | 59.3 | 3.9 | 5.2 |   | 263 |
| 10 | 3-Cl,4-F | 55.5 | 3.2 | 5.0 | 115–116 | 281 |
|   |   | 54.9 | 2.9 | 5.0 |   | 281 |

EXAMPLE 11

Preparation of 6-(3-α,α,α-trifluoromethylphenoxy) picolinic acid

A solution of methyl-6-(3-α,α,α-trifluoromethylphenoxy)-picolinate (8 g) in 50% aqueous methanol (45 ml) containing sodium hydroxide (2.5 g) was refluxed for 3 hours. The methanol was evaporated, more water added to the residue and the aqueous solution extracted with diethyl ether. The aqueous phase was then acidified with dilute hydrochloric acid to precipitate the title compound (7.1 g) as a white solid of melting point 92°–93° C.

m/e Theory: Found 283:283

| Theory for $C_{13}H_8NO_3F_3$: | C 55.1 | H 2.8 | N 4.9% |
|---|---|---|---|
| Found: | C 53.3 | H 3.0 | N 5.0% |

The compounds of general formula XX listed in Table 2 below were prepared by the method of Example 11.

TABLE 2

(General Formula XX)

[Structure: Xn-phenyl-O-pyridine-COOH]

| Example No. | Xn | C (Calc. Found) | H (Calc. Found) | N (Calc. Found) | Melting Point (°C.) | m/e (Theory Found) |
|---|---|---|---|---|---|---|
| 12 | — | 67.0 | 4.2 | 6.5 | 100–101 | 215 |
|  |  | 66.8 | 4.6 | 5.7 |  | 215 |
| 13 | 2,4-diCl | 55.1 | 2.8 | 4.9 | 92–93 | 283 |
|  |  | 53.3 | 3.0 | 5.0 |  | 283 |
| 14 | 3-$C_2H_5$ | 69.1 | 5.3 | 5.8 | not | 243 |
|  |  | 68.7 | 5.0 | 5.6 | recorded | 243 |
| 15 | 3,5-diCl | 50.9 | 2.5 | 4.9 | 140–141 | 283 |
|  |  | 51.0 | 2.9 | 5.8 |  | 283 |
| 16 | 3-O—$CH_2$—CH=$CH_2$ | 66.4 | 4.8 | 5.2 | 83–84 | 271 |
|  |  | 63.7 | 4.2 | 5.7 |  | 271 |
| 17 | 3-$NO_2$ | 55.4 | 3.1 | 10.8 | 147–149 | 260 |
|  |  | 54.4 | 2.6 | 10.8 |  | 260 |
| 18 | 3-$OCF_3$ | 52.2 | 2.7 | 4.7 | oil | 299 |
|  |  | 50.0 | 2.6 | 4.6 |  | 299 |
| 19 | 3-Cl | 57.8 | 3.2 | 5.6 | 84–85 | 249 |
|  |  | 57.4 | 3.0 | 5.5 |  | 249 |
| 20 | 3-Cl,4-F | 53.9 | 2.6 | 5.2 | 95–96 | 267 |
|  |  | 51.5 | 2.5 | 4.8 |  | 267 |

EXAMPLE 21

Preparation of N-(2,4-difluorophenyl)-2-chloro-6-pyridinecarboxamide

6-Chloropicolinic acid (25 g) in thionyl chloride (50ml) was stirred and heated to reflux for 1.5 hours. The excess thionyl chloride was evaporated in vacuo and dichloromethane (100 ml) added to the residual 6-chloropicolinoyl chloride. A solution of 2,4-difluoroaniline (20.5 g) and triethylamine (16 g) in dichloromethane (50 ml) was added with stirring, maintaining the temperature below 20° C. After the addition, the reaction mixture was stirred a further 1 hour at ambient temperature. Water was then added to the reaction mixture and the dichloromethane phase separated. After a further washing with water, brine and drying over anhydrous magnesium sulphate, the dichloromethane was removed to give the title compound (42 g) as a pale yellow solid of melting point 86°–87° C.

m/e Theory : Found 268:268

| Theory for $C_{12}H_7N_2OF_2Cl$: | C 53.7 | H 2.6 | N 10.4% |
|---|---|---|---|
| Found: | C 53.6 | H 2.7 | N 10.5% |

The compounds of general formula IV listed in Table 3 below were prepared by the method of Example 21.

TABLE 3

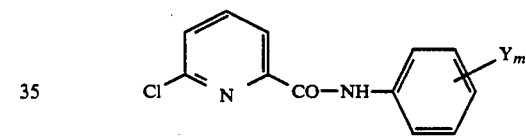

(General Formula IV; $R^1$ and $R^3$ are H; Hal is Cl; q is 0)

| Example No. | $Y_m$ | C (Calc. Found) | H (Calc. Found) | N (Calc. Found) | Melting Point (°C.) | m/e (Theory Found) |
|---|---|---|---|---|---|---|
| 22 | 4-F | 57.6 | 3.2 | 11.2 | 93–94 | 250 |
|  |  | 57.4 | 3.3 | 11.1 |  | 250 |
| 23 | 2-F | 57.6 | 3.2 | 11.2 | 117–118 | 250 |
|  |  | 58.6 | 3.2 | 11.2 |  | 250 |

EXAMPLE 24

Preparation of N-(2,4-difluorophenyl)-2-(3-α,α,α-trifluoromethylphenoxy)-6-pyridinecarboxamide 6-(3-α,α,α-Trifluoromethylphenoxy)picolinic acid (7.1 g) in thionyl chloride (50 ml) was refluxed for 1 hour. The excess thionyl chloride was evaporated in vacuo and dichloromethane added to the residual picolinoyl chloride. A solution of 2,4-difluoroaniline (3.3 g) and triethylamine (2.6 g) in dichloromethane (50 ml) was then added dropwise with stirring at ambient temperature. After stirring a further 1 hour, the reaction mixture was washed with water, dried over anhydrous magnesium sulphate and the dichloromethane evaporated. The residue was purified on a silica gel column using dichloromethane as eluant to give the title compound (6.9 g) as a white solid of melting point 110°–111° C.

m/e Theory: Found 394:394

| Theory for $C_{19}H_{11}N_2O_2F_5$: | C 57.9 | H 2.8 | N 7.1% |
| --- | --- | --- | --- |
| Found: | C 57.8 | H 2.9 | N 7.2% |

EXAMPLE 25

Preparation of N-(2,4-difluorophenyl)-2-(3-chlorophenoxy)-6-pyridinecarboxamide

A solution of sodium methoxide (from 0.26 g sodium in 10 ml methanol) was added to a solution of 3-chlorophenol (1.4 g) in xylene (20 ml). The solvents were evaporated in vacuo to give the dry sodium phenolate. Pyridine (10 ml) and xylene (20 ml) were added, followed by cuprous chloride (0.3 g) and the mixture heated to reflux. A solution of N-(2,4-difluorophenyl)-2-chloro-6-pyridinecarboxamide (2.6 g) in xylene (10 ml) was added dropwise and the mixture refluxed for a further 13 hours. After cooling, the mixture was poured into water (100 ml) and acidified with dilute hydrochloric acid. The organic phase was separated and the aqueous phase dried over anhydrous magnesium sulphate and evaporated. The residue was purified on a silica gel column using dichloromethane as eluant to give the title compound (2.5 g). Recrystallisation from 40–60 petroleum ether gave the title compound as a white solid of melting point 116°–117° C.

m/e Theory: Found 360:360

| Theory for $C_{18}H_{11}N_2O_2FCl$: | C 60.0 | H 3.0 | N 7.8% |
| --- | --- | --- | --- |
| Found: | C 60.5 | H 3.7 | N 7.9% |

EXAMPLE 26

Preparation of N-benzyl-2-(3,5-dichlorophenoxy)-6-pyridinecarboxamide

The title compound, an oil, was prepared in analogous manner to Example 24, using 6-(3,5-dichlorophenoxy)picolinoyl chloride and benzylamine.

m/e Theory: Found 372:372

| Theory for $C_{19}H_{14}N_2O_2Cl_2$: | C 61.3 | H 3.8 | N 7.5% |
| --- | --- | --- | --- |
| Found: | C 60.1 | H 3.8 | N 7.5% |

The compounds of general formula I listed in Table 4 below were prepared using an appropriate method of those exemplified in Examples 24 to 26, from starting materials as prepared in Examples 11 to 23.

TABLE 4

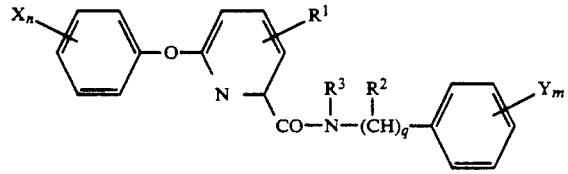

(General Formula I; Z is O)

| Ex. No. | $X_n$ | $Y_m$ | $R^1$ | $R^2$ | $R^3$ | q | C (Calc. Found) | H (Calc. Found) | N (Calc. Found) | Melting Point (°C.) | m/e (Theory Found) |
| --- | --- | --- | --- | --- | --- | --- | --- | --- | --- | --- | --- |
| 27 | — | 2,4-diF | H | — | H | 0 | 66.3 / 66.7 | 3.7 / 3.8 | 8.6 / 8.6 | 104–105 | 326 / 326 |
| 28 | 3-OCH₃ | 2,4-diF | H | — | H | 0 | 64.0 / 63.6 | 3.9 / 3.9 | 7.8 / 7.6 | 71–73 | 356 / 356 |
| 29 | 3-CH₃ | 2,4-diF | H | — | H | 0 | 67.0 / 66.5 | 4.1 / 4.1 | 8.2 / 7.9 | 95–96 | 340 / 340 |
| 30 | 3-CN | 2,4-diF | H | — | H | 0 | 64.9 / 63.8 | 3.1 / 3.8 | 11.9 / 11.9 | 155–156 | 351 / 351 |
| 31 | 3-F | 2,4-diF | H | — | H | 0 | 62.8 / 63.6 | 3.2 / 3.2 | 8.1 / 8.2 | 109–110 | 344 / 344 |
| 32 | 4-F | 2,4-diF | H | — | H | 0 | 62.8 / 62.4 | 3.2 / 2.9 | 8.1 / 8.1 | 127–128 | 344 / 344 |
| 33 | 3-CF₃ | 4-F | H | — | H | 0 | 60.6 / 60.4 | 3.2 / 3.1 | 7.4 / 7.5 | 102–103 | 376 / 376 |
| 34 | 3-Cl | 4-F | H | — | H | 0 | 63.2 / 62.8 | 3.5 / 3.5 | 8.2 / 8.2 | 112–113 | 342 / 342 |
| 35 | 3-CN | 4-F | H | — | H | 0 | 68.5 / 67.9 | 3.6 / 3.8 | 12.6 / 12.6 | 128–129 | 333 / 333 |
| 36 | 3-F | 4-F | H | — | H | 0 | 66.3 / 65.0 | 3.7 / 3.1 | 8.6 / 8.2 | 73–75 | 326 / 326 |
| 37 | 3-CF₃,4-Cl | 4-F | H | — | H | 0 | 55.6 / 55.4 | 2.7 / 2.6 | 6.8 / 6.9 | 142–143 | 410 / 410 |
| 38 | 3-CH₃ | 4-F | H | — | H | 0 | 70.8 / 68.5 | 4.7 / 4.4 | 8.7 / 8.5 | 83–84 | 322 / 322 |
| 39 | 3,4-diF | 2,4-diF | H | — | H | 0 | 59.6 / 57.9 | 2.7 / 3.3 | 7.7 / 7.7 | 120–121 | 362 / 362 |
| 40 | 3-CF₃ | 2-F | H | — | H | 0 | 60.6 / 59.9 | 3.2 / 3.3 | 7.4 / 7.2 | 102–104 | 376 / 376 |
| 41 | 3-CF₃ | 2-F,4-Cl | H | — | H | 0 | 55.6 / 54.4 | 2.7 / 2.8 | 6.8 / 7.1 | 85–87 | 410 / 410 |
| 42 | 3-CO₂CH₃ | 4-F | H | — | H | 0 | 65.6 / 64.8 | 4.1 / 4.6 | 7.7 / 8.2 | 119–120 | 366 / 366 |
| 43 | 3-CF₃ | 2,4-diCl | H | — | H | 0 | 53.5 / 52.7 | 2.6 / 2.9 | 6.6 / 7.0 | 111–113 | 426 / 426 |
| 44 | 3-CF₃ | 2-F,5-CH₃ | H | — | H | 0 | 61.5 | 3.6 | 7.2 | 90–93 | 390 |

TABLE 4-continued (General Formula I; Z is O)

| Ex. No. | $X_n$ | $Y_m$ | $R^1$ | $R^2$ | $R^3$ | q | C (Calc. Found) | H (Calc. Found) | N (Calc. Found) | Melting Point (°C.) | m/e (Theory Found) |
|---|---|---|---|---|---|---|---|---|---|---|---|
| | | | | | | | 60.5 | 3.9 | 7.2 | | 390 |
| 45 | 3-CF$_3$ | 2,6-diF | H | — | H | 0 | 57.9 | 2.8 | 7.1 | 126–127 | 394 |
| | | | | | | | 56.8 | 3.0 | 7.1 | | 394 |
| 46 | 3-CF$_3$ | 3-F | H | — | H | 0 | 60.6 | 3.2 | 7.4 | 63–66 | 376 |
| | | | | | | | 60.3 | 3.5 | 7.0 | | 376 |
| 47 | 3-CF$_3$ | 2-F,4-I | H | — | H | 0 | 45.4 | 2.2 | 5.6 | 105–106 | 502 |
| | | | | | | | 43.2 | 2.6 | 5.7 | | 502 |
| 48 | 3-CF$_3$ | 2-F,5-NO$_2$ | H | — | H | 0 | 54.2 | 2.6 | 10.0 | 160–162 | 421 |
| | | | | | | | 53.6 | 2.6 | 10.2 | | 421 |
| 49 | 3-Cl | 2-F | H | — | H | 0 | 63.2 | 3.5 | 8.2 | 105–107 | 342 |
| | | | | | | | 62.3 | 3.6 | 8.3 | | 342 |
| 50 | 3-CONH$_2$ | 2,4-diF | H | — | H | 0 | 61.8 | 3.5 | 11.4 | 185–186 | 369 |
| | | | | | | | 59.1 | 4.0 | 11.0 | | 369 |
| 51 | 3-C$_2$H$_5$ | 4-F | H | — | H | 0 | 71.4 | 5.1 | 8.3 | 64–65 | 336 |
| | | | | | | | 69.9 | 5.4 | 8.6 | | 336 |
| 52 | 3-C$_2$H$_5$ | 2,4-diF | H | — | H | 0 | 67.8 | 4.5 | 7.9 | 70–71 | 354 |
| | | | | | | | 66.3 | 4.6 | 8.2 | | 354 |
| 53 | 3-CF$_3$ | — | H | — | H | 0 | 63.7 | 3.6 | 7.8 | 89–90 | 358 |
| | | | | | | | 63.5 | 3.7 | 8.0 | | 358 |
| 54 | 3-OCH$_3$ | 2-F | H | — | H | 0 | 67.5 | 4.4 | 8.3 | 89–91 | 338 |
| | | | | | | | 67.5 | 4.5 | 8.8 | | 338 |
| 55 | 3-CF$_3$ | 4-CH$_3$ | H | — | H | 0 | 64.5 | 4.0 | 7.5 | 82–83 | 372 |
| | | | | | | | 64.4 | 4.2 | 8.3 | | 372 |
| 56 | 3-CF$_3$ | 4-CF$_3$ | H | — | H | 0 | 56.3 | 2.8 | 6.6 | 131–132 | 426 |
| | | | | | | | 57.1 | 3.2 | 7.0 | | 426 |
| 57 | 3-CF$_3$ | 2,4,5-triF | H | — | H | 0 | 55.3 | 2.4 | 6.8 | 106–107 | 412 |
| | | | | | | | 56.3 | 2.6 | 7.0 | | 412 |
| 58 | 3-CF$_3$ | 4-Cl | H | — | H | 0 | 58.1 | 3.1 | 7.1 | 91–92 | 392 |
| | | | | | | | 58.3 | 3.1 | 7.8 | | 392 |
| 59 | 3-CF$_3$ | 2,4-di(CH$_3$) | H | — | H | 0 | 65.3 | 4.4 | 7.3 | 141–142 | 386 |
| | | | | | | | 64.2 | 4.5 | 7.8 | | 386 |
| 60 | 3-CF$_3$ | 4-CN | H | — | H | 0 | 62.7 | 3.1 | 11.0 | 115–116 | 383 |
| | | | | | | | 62.8 | 3.3 | 11.0 | | 383 |
| 61 | 3,5-diCl | 2,4-diF | H | — | H | 0 | 54.8 | 2.5 | 7.1 | 122–123 | 394 |
| | | | | | | | 53.1 | 2.4 | 6.6 | | 394 |
| 62 | 3,5-diCl | 4-F | H | — | H | 0 | 57.4 | 2.9 | 7.4 | 149–150 | 376 |
| | | | | | | | 57.2 | 2.5 | 6.7 | | 376 |
| 63 | 3-Cl,4-F | 2,4-diF | H | — | H | 0 | 57.1 | 2.6 | 7.4 | 144–145 | 378 |
| | | | | | | | 55.8 | 2.7 | 7.0 | | 378 |
| 64 | 3-Cl,4-F | 4-F | H | — | H | 0 | 60.0 | 3.1 | 7.8 | 133–134 | 360 |
| | | | | | | | 58.3 | 2.9 | 7.3 | | 360 |
| 65 | 3-O—CH$_2$CH=CH$_2$ | 4-F | H | — | H | 0 | 69.2 | 4.7 | 7.7 | 91–93 | 364 |
| | | | | | | | 64.6 | 4.5 | 7.7 | | 364 |
| 66 | 3-NO$_2$ | 4-F | H | — | H | 0 | 61.2 | 3.4 | 11.9 | 155–156 | 353 |
| | | | | | | | 60.5 | 3.4 | 11.9 | | 353 |
| 67 | 3-OCF$_3$ | 4-F | H | — | H | 0 | 58.2 | 3.1 | 7.1 | 103–104 | 392 |
| | | | | | | | 56.9 | 2.6 | 6.7 | | 392 |
| 68 | 3-O—CH$_2$CH=CH$_2$ | 2,4-diF | H | — | H | 0 | 66.0 | 4.2 | 7.3 | 60–63 | 382 |
| | | | | | | | 64.0 | 3.9 | 7.0 | | 382 |
| 69 | 3-CO$_2$H | 2,4-diF | H | — | H | 0 | 61.6 | 3.2 | 7.6 | 210–212 | 370 |
| | | | | | | | 61.8 | 4.0 | 7.2 | | 370 |
| 70 | 3-CON(CH$_3$)$_2$ | 2,4-diF | H | — | H | 0 | 63.5 | 4.3 | 10.6 | 122–123 | 397 |
| | | | | | | | 63.2 | 4.4 | 10.4 | | 397 |
| 71 | 3-COSC$_2$H$_5$ | 2,4-diF | H | — | H | 0 | 60.9 | 3.9 | 6.7 | 97–98 | 414 |
| | | | | | | | 60.9 | 3.9 | 7.0 | | 414 |
| 72 | 3-CF$_3$ | 4-F | 5-Cl | — | H | 0 | 55.6 | 2.7 | 6.8 | 96–98 | 410 |
| | | | | | | | 55.5 | 3.2 | 6.6 | | 410 |
| 73 | 3-CF$_3$ | — | H | — | allyl | 0 | 66.3 | 4.3 | 7.0 | oil | 398 |
| | | | | | | | 64.9 | 4.4 | 6.9 | | 398 |
| 74 | 3-CF$_3$ | 2-F | H | H | H | 1 | 61.5 | 3.6 | 7.2 | oil | 390 |
| | | | | | | | 61.2 | 3.9 | 7.1 | | 390 |
| 75 | 3-CF$_3$ | 3-F | H | H | H | 1 | 61.5 | 3.6 | 7.2 | oil | 390 |
| | | | | | | | 59.9 | 3.7 | 7.0 | | 390 |
| 76 | 3-CF$_3$ | 4-F | H | H | H | 1 | 61.5 | 3.6 | 7.2 | oil | 390 |
| | | | | | | | 58.5 | 3.5 | 6.8 | | 390 |
| 77 | 3-NO$_2$ | 2,4-diF | H | — | H | 0 | 58.2 | 3.0 | 11.3 | 151–153 | 371 |
| | | | | | | | 57.9 | 3.1 | 11.2 | | 371 |
| 78 | 3-CF$_3$ | — | H | — | CH$_3$ | 0 | 64.5 | 4.0 | 7.5 | oil | 372 |

TABLE 4-continued (General Formula I; Z is O)

| Ex. No. | $X_n$ | $Y_m$ | $R^1$ | $R^2$ | $R^3$ | q | C (Calc. Found) | H (Calc. Found) | N (Calc. Found) | Melting Point (°C.) | m/e (Theory Found) |
|---|---|---|---|---|---|---|---|---|---|---|---|
| 79 | 3-CF₃ | — | H | CH₃ (racemic) | H | 1 | 65.3 65.1 | 4.2 4.4 4.4 | 7.5 7.3 7.1 | 85–86 | 372 386 386 |
| 80 | 3-CF₃ | — | H | CH₃ [S] | H | 1 | 65.3 65.5 | 4.4 4.6 | 7.3 7.5 | oil | 386 386 |
| 81 | 3-CF₃ | — | H | CH₃ [R] | H | 1 | 65.3 64.5 | 4.4 4.3 | 7.3 7.4 | oil | 386 386 |
| 82 | 3-CF₃ | 4-OCH₃ | H | — | H | 0 | 61.9 62.1 | 3.9 4.2 | 7.2 7.1 | 100–102 | 388 388 |
| 83 | 3-CF₃ | 4-NO₂ | H | — | H | 0 | 56.6 57.4 | 3.0 3.7 | 10.4 10.3 | 143–144 | 403 403 |
| 84 | 3-CF₃ | 4-OCF₃ | H | — | H | 0 | 54.3 54.2 | 2.7 3.0 | 6.3 6.4 | 112–113 | 442 442 |
| 85 | 3-CF₃ | — | H | — | C₂H₅ | 0 | 65.3 65.5 | 4.4 4.7 | 7.3 7.3 | oil | 386 386 |
| 86 | 3-CF₃ | — | H | H | CH₃ | 1 | 65.3 64.1 | 4.4 4.5 | 7.3 7.2 | oil | 386 386 |
| 87 | 3-Br | 4-F | H | — | H | 0 | 55.8 58.6 | 3.1 3.5 | 7.2 7.8 | 121–122 | 387 387 |
| 88 | 3,4-diCl | 4-F | H | — | H | 0 | 57.4 56.9 | 2.9 3.0 | 7.4 7.3 | 124–125 | 376 376 |
| 89 | 3-Br | 2,4-diF | H | — | H | 0 | 53.3 56.6 | 2.7 3.0 | 6.9 7.2 | 117–118 | 405 405 |
| 90 | 3,4-diCl | 2,4-diF | H | — | H | 0 | 54.8 54.3 | 2.5 2.7 | 7.1 6.8 | 142–143 | 394 394 |
| 91 | 3-CF₃,4-F | 4-F | H | — | H | 0 | 57.8 57.4 | 2.8 3.0 | 7.1 7.0 | 129–131 | 394 394 |
| 92 | 3-OCF₃ | 2,3,4-triF | H | — | H | 0 | 53.3 52.8 | 2.3 2.5 | 6.5 6.5 | 95–96 | 428 428 |
| 93 | 4-CH₃ | 2,4-diF | H | — | H | 0 | 67.1 67.0 | 4.1 4.1 | 8.2 8.1 | 103–104 | 340 340 |
| 94 | 3-OCF₃ | 2-F,3-CF₃ | H | — | H | 0 | 52.2 51.7 | 2.4 2.6 | 6.1 6.0 | 88–89 | 460 460 |
| 95 | 4-SCH₃ | 4-F | H | — | H | 0 | 64.4 62.3 | 4.2 4.1 | 7.9 8.3 | 113–114 | 354 354 |
| 96 | — | — | H | — | H | 0 | 74.5 73.8 | 4.8 4.6 | 9.7 9.5 | not recorded | 290 290 |
| 97 | 3-Cl | 2,6-diC₂H₅ | H | — | H | 0 | 69.5 69.8 | 5.5 5.6 | 7.4 7.3 | 81–82 | 380 380 |
| 98 | 3-Cl | 2,6-diCH₃ | H | — | H | 0 | 68.2 67.8 | 4.8 4.9 | 8.0 7.8 | 98–99 | 352 352 |
| 99 | 3-CF₃ | 4-NO₂ | H | — | CH₃ | 0 | 57.6 57.9 | 3.4 3.7 | 10.1 10.2 | 93–94 | 417 417 |
| 100 | 3-CF₃ | 4-Cl | H | — | CH₃ | 0 | 59.1 59.0 | 3.4 3.7 | 6.9 6.9 | 88–89 | 406 406 |
| 101 | 3-CF₃ | 4-OCH₃ | H | — | CH₃ | 0 | 62.7 62.9 | 4.2 4.5 | 7.0 7.0 | 69–70 | 402 402 |
| 102 | 3-CF₃ | 2-CH₃ | H | H | H | 1 | 65.3 65.5 | 4.4 4.7 | 7.3 7.4 | 61–62 | 386 386 |
| 103 | 3-CF₃ | 3-CH₃ | H | H | H | 1 | 65.3 65.4 | 4.4 4.7 | 7.3 7.4 | 54–55 | 386 386 |
| 104 | 3-CF₃ | 4-CH₃ | H | H | H | 1 | 65.3 64.7 | 4.4 4.2 | 7.3 7.2 | 105–106 | 386 386 |
| 105 | 3-CF₃ | 2-CH₃,3-Cl | H | — | H | 0 | 59.1 59.6 | 3.4 3.9 | 6.9 7.3 | 126–127 | 406 406 |
| 106 | 3-CF₃ | 2,3-diCH₃ | H | — | H | 0 | 65.3 65.4 | 4.4 4.8 | 7.2 7.3 | 140–141 | 386 386 |
| 107 | 3-CF₃ | 2-F, 3-Cl, 4-F, 5-Cl | H | — | H | 0 | 49.3 49.1 | 1.9 2.3 | 6.1 6.0 | 136–137 | 462 462 |

It is, of course, possible to prepare the compounds of the present invention directly by reaction of an ester of an appropriate phenoxypicolinic acid with an appropriate aniline or aralkylamine, as exemplified in Example 108 below, in which the compound of Example 53 is prepared by direct reaction of ester and aniline.

Preparation of N-phenyl-2-(3-α,α,α-trifluoromethylphenoxy)-6-pyridinecarboxamide Methyl-6- (3,α,α,α-trifluoromethylphenoxy) picolinate (1 g) and aniline (1 ml) were heated to reflux for 3 hours. After cooling, methylene chloride was added to the residue and the solution washed with water, brine and dried over anhydrous magnesium sulphate. The dichloromethane was evaporated off and the residue purified on a silica gel column using 54 (v/v) diethyl ether-dichloromethane as eluant to give the title compound (1.1 g) of melting point 89°–90° C.

m/e Theory: Found 358:358

| Theory for $C_{19}H_{13}N_2O_2F_3$: | C 63.7 | H 3.6 | N 7.8% |
|---|---|---|---|
| Found: | C 63.5 | H 3.7 | N 8.0% |

EXAMPLE 109

Preparation of N-(4-methylphenyl)-2-(3-α,α,α-trifluoromethylphenoxy)-6-pyridinethiocarboxamide A mixture of N-(4-methylphenyl)-2-(3-α,α,α-trifluoromethylphenoxy)-6-pyridinecarboxamide (1.3 g) and phosphorus pentasulphide (1.5 g) in dry pyridine (50 ml) was refluxed for 4 hours. The hot reaction mixture was then poured onto ice (50 g) and the aqueous solution extracted with dichloromethane. The combined extracts were washed with 2M hydrochloric acid and water. After drying over anhydrous magnesium sulphate, the dichloromethane was evaporated off. The residual solid was purified using a silica gel column using dichloromethane as eluant to give the title compound (0.6 g) as a yellow solid of melting point 120°–121° C.

m/e Theory: Found 388:388

| Theory for $C_{20}H_{15}ON_2F_3S$: | C 61.9 | H 3.9 | N 7.2% |
|---|---|---|---|
| Found: | C 61.3 | H 3.9 | N 7.3% |

EXAMPLE 110

Preparation of N-(4-fluorophenyl)-2-(3-α,α,α-trifluoromethylphenoxy)-6-pyridinethiocarboxamide The title compound was prepared in analogous manner to the procedure of Example 109 from N-(4-fluorophenyl)-2-(3-α,α,α-trifluoromethylphenyl)-6-pyridinecarboxamide. Melting point: 96°–97° C.

m/e Theory: Found 392:392

| Theory for $C_{19}H_{12}ON_2F_4S$: | C 58.2 | H 3.1 | N 7.1% |
|---|---|---|---|
| Found: | C 58.4 | H 3.4 | N 7.1% |

EXAMPLE 111

Preparation of N-(2,4-difluorophenyl)-2-(3-[1'-ethoxyiminoethyl]-phenoxy)-6-pyridinecarboxamide A solution of N-(2,4-dichlorophenyl)-2-(3-acetylphenoxy)-6-pyridinecarboxamide (0.76 g), O-ethylhydroxylamine hydrochloride (0.22 g) and triethylamine (0.23 g) in ethanol (50 ml) was refluxed for 6 hours. The ethanol was removed in vacuo and the residue purified on a silica gel column using methylene dichloride as eluant to give the title compound (0.3 g) as a white solid of melting point 104°–105° C.

m/e Theory: Found 411:411

| Theory for $C_{22}H_{19}O_3N_3F_2$: | C 64.2 | H 4.6 | N 10.2% |
|---|---|---|---|
| Found: | C 60.0 | H 3.9 | N 9.8% |

EXAMPLE 112

Preparation of N-(4-fluorophenyl)-2-(4-methylsulphonylphenoxy)-6-pyridinecarboxamide Metachloroperoxybenzoic acid (2.04 g, (50%)) was added to a solution of N-(4-fluorophenyl)-2-(4-methylmercaptophenoxy)-6-pyridinecarboxamide (1.0 g) in methylene dichloride. The reaction mixture was stirred overnight at room temperature. The dichloromethane was evaporated off and the residue purified on a silica gel column using 2.5% (v/v) diethylether-dichloromethane to give the title compound (0.7 g) as a white solid of melting point 134°–135° C.

m/e Theory: Found 386:386

| Theory for $C_{19}H_{15}O_4N_2SF$: | C 59.1 | H 3.9 | N 7.3% |
|---|---|---|---|
| Found: | C 59.1 | H 4.0 | N 7.2% |

Herbicidal Activity

To evaluate their herbicidal activity, compounds according to the invention were tested using as representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plants specified above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 900 litres per hectare in the soil spray and foliar spray test, and at a dosage of level equivalent to 10 kilograms of active material per hectare in a volume equivalent to approximately 3,000 litres per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table II below. In the Table, a blank space indicates a rating 0, and an asterisk indicates that no result was obtained.

TABLE 5

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 24 | 4 | 2 | 5 | 4 | 3 | 2 | 2 | 2 | 5 | 5 | 4 | 7 | 5 | 6 | 7 | 9 | 6 | 4 | 2 | 8 | 5 | 3 | 6 | 8 | |
| | | | | | | | | | 1 | 4 | 3 | 7 | 4 | 5 | 7 | 9 | 6 | 3 | 1 | 8 | 4 | 2 | 6 | 8 | |
| 25 | | | 2 | | 2 | 3 | 2 | 1 | 5 | 4 | 1 | 6 | 3 | 4 | 8 | 8 | 5 | 1 | | 5 | | 2 | 5 | 6 | |
| | | | | | | | | | 1 | 3 | | 4 | 1 | 3 | 7 | 8 | 4 | | | 4 | | 1 | 4 | 3 | |
| 26 | | | | | | 2 | | | 5 | 4 | | 6 | 3 | 2 | 7 | 6 | 3 | | | | | | | | |
| | | | | | | | | | 1 | 2 | | 1 | 1 | 1 | 5 | 3 | 3 | | | | | | | | |
| 27 | 2 | | 2 | | 3 | 3 | 3 | 1 | 5 | 5 | 3 | 5 | 4 | 5 | 8 | 6 | 6 | | | 5 | | | 4 | 2 | |
| | | | | | | | | | 1 | 2 | 1 | 4 | 2 | 4 | 8 | 6 | 5 | | | 3 | | | 2 | 1 | |
| 28 | | | 1 | | 1 | 5 | | | 5 | 3 | | 5 | 2 | * | * | * | 4 | | | 4 | | | 3 | 2 | |
| | | | | | | | | | 1 | 3 | | 5 | 2 | 5 | 6 | 8 | 4 | | | 2 | | | 3 | | |
| 29 | 1 | | 4 | 1 | 2 | 2 | 2 | | 5 | 5 | 3 | 8 | 4 | 5 | 8 | 8 | 5 | | | 6 | 1 | 1 | 5 | 5 | |
| | | | | | | | | | 1 | 4 | 2 | 8 | 2 | 4 | 8 | 8 | 4 | | | 5 | | | 5 | 4 | |
| 30 | 2 | | 2 | 1 | 1 | 2 | 3 | 1 | 5 | 3 | 2 | 6 | 3 | 5 | * | 8 | 4 | | | 2 | | 1 | 5 | 6 | |
| | | | | | | | | | 1 | 3 | 2 | 4 | 2 | 4 | 8 | 8 | 4 | | | | | | 4 | 4 | |
| 31 | 2 | | | | 1 | 3 | 3 | 1 | 5 | 4 | 1 | 7 | 3 | * | * | * | 4 | 2 | | 7 | 1 | 1 | 5 | 5 | |
| | | | | | | | | | 1 | 2 | 1 | 6 | 2 | 4 | 8 | 7 | 4 | 1 | | 5 | | | 4 | 3 | |
| 32 | | | | 1 | 2 | | | | 5 | 2 | 1 | 5 | 2 | 4 | * | * | 5 | | | 5 | | | 5 | 4 | |
| | | | | | | | | | 1 | 2 | 1 | 3 | 2 | 4 | 9 | 7 | 5 | | | 3 | | | 4 | 2 | |
| 33 | 1 | 3 | 6 | 5 | 4 | 6 | 6 | 2 | 5 | 5 | 5 | 8 | 6 | 6 | 9 | 9 | 6 | 4 | 6 | 8 | 6 | 4 | 8 | 9 | 1 |
| | | | | | | | | | 1 | 5 | 5 | 8 | 6 | 6 | 9 | 9 | 6 | 3 | 4 | 7 | 6 | 3 | 8 | 9 | |
| 34 | 3 | 1 | 4 | 2 | 2 | 4 | 2 | | 5 | 3 | 3 | 8 | 3 | 6 | 9 | 9 | 5 | 1 | 1 | 7 | 2 | 3 | 7 | 7 | |
| | | | | | | | | | 1 | 3 | 3 | 8 | 3 | 5 | 9 | 9 | 5 | 1 | | 6 | | 2 | 5 | 7 | |
| 35 | 4 | 4 | 3 | 4 | 4 | 5 | 4 | | 5 | 4 | 3 | 6 | 3 | 5 | 9 | 9 | 6 | 2 | 2 | 6 | 3 | 5 | 8 | 8 | 3 |
| | | | | | | | | | 1 | 4 | 3 | 5 | 2 | 4 | 9 | 9 | 5 | 2 | 2 | 5 | 3 | 4 | 8 | 8 | 3 |
| 36 | 5 | 2 | 6 | 3 | 2 | 5 | 4 | | 5 | 6 | 4 | 7 | 5 | 6 | 7 | 7 | 7 | 4 | 1 | 8 | 3 | 3 | 8 | 8 | 2 |
| | | | | | | | | | 1 | 5 | 2 | 7 | 3 | 5 | 7 | 7 | 6 | 3 | 1 | 8 | 1 | 2 | 8 | 8 | 2 |
| 37 | | | 2 | | | 3 | 4 | 4 | 5 | 5 | 3 | 6 | 4 | 4 | 8 | 7 | 6 | 1 | 4 | 5 | | | 6 | 7 | |
| | | | | | | | | | 1 | 3 | 2 | 4 | 2 | 4 | 8 | 7 | 5 | | 3 | 4 | | | 6 | 7 | |
| 38 | 3 | 1 | 4 | 2 | 1 | 3 | 2 | 1 | 5 | 5 | 4 | 8 | 4 | 5 | 8 | 6 | 8 | 1 | | 8 | 1 | 2 | 7 | 8 | 2 |
| | | | | | | | | | 1 | 4 | 3 | 8 | 3 | 5 | 8 | 6 | 7 | | | 7 | | | 6 | 8 | 1 |
| 39 | 2 | 2 | 4 | 3 | 2 | 5 | 3 | | 5 | 4 | 1 | 7 | 3 | 5 | 8 | 9 | 5 | | | 4 | | | 4 | 3 | |
| | | | | | | | | | 1 | 4 | | 5 | 2 | 5 | 8 | 9 | 5 | | | 1 | | | 2 | 1 | |
| 40 | | 2 | 4 | 6 | 2 | 2 | 3 | | 5 | 6 | 3 | 7 | 5 | 6 | 8 | 9 | 7 | 2 | 3 | 8 | 5 | 3 | 8 | 7 | |
| | | | | | | | | | 1 | 3 | 2 | 7 | 4 | 5 | 8 | 9 | 7 | 1 | 1 | 8 | 4 | 2 | 6 | 5 | |
| 41 | | | | | | | | | 5 | 4 | | 7 | 4 | 3 | 7 | 7 | 5 | | | 1 | | | 5 | 5 | 3 |
| | | | | | | | | | 1 | 3 | | 6 | 2 | 3 | 7 | 7 | 5 | | | | | | 5 | 4 | 2 |
| 42 | 1 | | 1 | | 1 | 2 | 2 | | 5 | 4 | 1 | 4 | 2 | 3 | 7 | 6 | 4 | | | | | | 3 | 4 | |
| | | | | | | | | | 1 | 3 | | 1 | | 3 | 6 | 5 | 3 | | | | | | 1 | 1 | |
| 43 | | | | | | | | | 5 | 3 | | 3 | 3 | 3 | 8 | 7 | 5 | | | | | | 2 | 1 | |
| | | | | | | | | | 1 | 2 | | 1 | 1 | 3 | 8 | 5 | 4 | | | | | | 1 | | |
| 44 | | * | 1 | 1 | 1 | 3 | 1 | 1 | 5 | 4 | 1 | 6 | 4 | 5 | 8 | 9 | 7 | | | 2 | | | 5 | 3 | |
| | | | | | | | | | 1 | 4 | | 5 | 2 | 5 | 8 | 9 | 7 | | | 1 | | | 4 | 2 | |
| 45 | 1 | * | | | 1 | 2 | | | 5 | 4 | 1 | 7 | 5 | 6 | 9 | 8 | 6 | | | 1 | | | 4 | 2 | |
| | | | | | | | | | 1 | 3 | | 5 | 4 | 5 | 9 | 8 | 5 | | | | | | 3 | 1 | |
| 46 | 4 | 4 | 4 | 5 | 1 | 2 | 3 | | 5 | 7 | 6 | 8 | 7 | 7 | 9 | 9 | 8 | 3 | 3 | 8 | 6 | 4 | 8 | 8 | 8 |
| | | | | | | | | | 1 | 5 | 5 | 8 | 6 | 7 | 9 | 9 | 7 | 3 | 2 | 8 | 5 | 3 | 8 | 7 | 3 |
| 47 | | | | | 1 | 3 | 1 | | 5 | 3 | | 4 | 3 | 3 | 8 | 8 | 4 | | | 2 | | 5 | 4 | 2 | |
| | | | | | | | | | 1 | 3 | | 3 | 1 | 2 | 8 | 6 | 4 | | | 1 | | 4 | 3 | | |
| 48 | | | 1 | 3 | 2 | 2 | | 2 | 5 | 5 | 1 | 5 | 4 | 3 | * | * | 2 | | | | | | 3 | 2 | 2 |
| | | | | | | | | | 1 | 3 | | 3 | 3 | 3 | 8 | 7 | 2 | | | | | | 3 | 2 | |
| 49 | | | 1 | 1 | 1 | 2 | 3 | | 5 | 3 | 1 | 5 | 4 | 6 | 8 | 7 | 5 | | | | | | 4 | 1 | |
| | | | | | | | | | 1 | 2 | | 5 | 2 | 6 | 8 | 7 | 5 | | | | | | 3 | | |
| 50 | | | | | | | | | 5 | 2 | | 2 | 1 | * | * | * | 3 | | | | | | | | |
| | | | | | | | | | 1 | 2 | | 1 | 1 | 3 | 5 | 4 | 3 | | | | | | | | |
| 51 | | | 3 | 2 | 1 | 2 | 1 | | 5 | 5 | 2 | 7 | 4 | 5 | 8 | 9 | 7 | | | 3 | 1 | | 6 | 4 | |
| | | | | | | | | | 1 | 4 | 2 | 7 | 3 | 5 | 8 | 9 | 7 | | | 1 | | | 5 | 2 | |
| 52 | | | 3 | 1 | 1 | 2 | 1 | 1 | 5 | 4 | 2 | 7 | 5 | 5 | 9 | 9 | 6 | | | 3 | | | 4 | 3 | |
| | | | | | | | | | 1 | 3 | 1 | 7 | 3 | 4 | 9 | 9 | 6 | | | 1 | | | 3 | 1 | |
| 53 | 2 | 4 | 6 | 6 | 2 | 4 | 4 | 2 | 5 | 5 | 6 | 8 | 7 | 7 | 9 | 9 | 7 | 4 | 4 | 8 | 6 | 6 | 8 | 8 | 7 |
| | | | | | | | | | 1 | 4 | 4 | 8 | 6 | 7 | 9 | 9 | 7 | 4 | 4 | 8 | 6 | 5 | 8 | 8 | 6 |
| 54 | | | 1 | | | | | | 5 | 7 | 1 | 5 | 3 | 4 | 8 | 7 | 6 | | | | | | | | |
| | | | | | | | | | 1 | 2 | | 2 | 2 | 4 | 7 | 5 | 5 | | | | | | | | |
| 55 | 3 | 1 | 4 | 4 | 2 | 3 | 2 | 1 | 5 | 6 | 5 | 8 | 5 | 7 | 8 | 9 | 7 | 1 | | 6 | 2 | 1 | 6 | 6 | |
| | | | | | | | | | 1 | 3 | 1 | 6 | 3 | 6 | 8 | 9 | 6 | | | 3 | 1 | | 5 | 5 | |
| 56 | | | | 1 | | 2 | 2 | 1 | 5 | 4 | | 6 | 3 | 5 | 9 | 9 | 8 | | | 3 | | | 6 | 4 | |
| | | | | | | | | | 1 | 3 | | 5 | 2 | 4 | 9 | 9 | 8 | | | 1 | | | 5 | 2 | |
| 57 | | 1 | 2 | 3 | | | 1 | | 5 | 6 | 3 | 8 | 6 | 7 | 9 | 9 | 7 | 3 | 1 | 7 | 5 | 3 | 7 | 7 | 2 |
| | | | | | | | | | 1 | 4 | 1 | 7 | 4 | 6 | 9 | 9 | 7 | 2 | 1 | 7 | 4 | 1 | 5 | 5 | |
| 58 | 2 | 1 | 4 | 3 | | 3 | 3 | | 5 | 5 | 3 | 8 | 5 | 5 | 9 | 9 | 7 | | | 4 | 2 | 1 | 6 | 6 | |
| | | | | | | | | | 1 | 4 | 1 | 6 | 3 | 5 | 9 | 9 | 7 | | | 3 | 1 | | 5 | 5 | |
| 59 | | | | | | 1 | | | 5 | 4 | | 4 | 3 | 3 | 8 | 8 | 5 | | | | | | | | |

TABLE 5-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 60 | | | 1 | | | 1 | 2 | | 1 | 3 | | 3 | 2 | 3 | 8 | 8 | 4 | | | | | | | | |
| | | | | | | | | | 5 | 4 | | 6 | 3 | 6 | 9 | 9 | 6 | | | 2 | | | 4 | 2 | |
| 61 | | | | | | | | | 1 | 3 | | 4 | 2 | 6 | 9 | 9 | 6 | | | 1 | | | 4 | 1 | |
| | | | | | | | | | 5 | 4 | | 4 | 3 | 3 | 7 | 6 | 4 | | | | | | 1 | | |
| 62 | | | | | | | | | 1 | 2 | | 1 | 2 | 3 | 7 | 4 | 3 | | | | | | 1 | | |
| | | | | | | | | | 5 | 4 | | 2 | 1 | 3 | 7 | 5 | 3 | | | | | | 1 | | |
| 63 | | | | | 1 | 2 | | | 1 | 2 | | 1 | 1 | 3 | 6 | 4 | 3 | | | | | | 1 | | |
| | | | | | | | | | 5 | 5 | | 6 | 3 | 4 | 8 | 8 | 5 | 2 | 2 | 5 | | | 5 | 5 | |
| 64 | 3 | 3 | 4 | 3 | 2 | 4 | 3 | | 1 | 3 | | 3 | 2 | 3 | 8 | 8 | 4 | | | 3 | | | 4 | 3 | |
| | | | | | | | | | 5 | 7 | 2 | 7 | 5 | 5 | 8 | 9 | 6 | | | 3 | | | 4 | 4 | 3 |
| 65 | | | 1 | 1 | 1 | 2 | 2 | | 1 | 5 | 2 | 5 | 3 | 5 | 8 | 9 | 6 | | | 2 | | | 3 | 3 | |
| | | | | | | | | | 5 | 6 | 2 | 7 | 5 | 4 | 8 | 7 | 5 | | | | | | | | |
| 66 | 2 | 1 | 2 | 2 | 1 | 2 | 2 | | 1 | 5 | 1 | 4 | 3 | 2 | 8 | 7 | 5 | | | | | | | | |
| | | | | | | | | | 5 | 4 | 2 | 6 | 4 | 4 | 9 | 9 | 4 | | | 1 | | 1 | 3 | 1 | |
| 67 | 4 | 4 | 5 | 6 | 3 | 2 | 1 | 2 | 1 | * | * | * | * | * | * | * | * | | | 1 | | | 2 | 1 | |
| | | | | | | | | | 5 | 6 | 5 | 8 | 7 | 7 | 9 | 9 | 7 | 3 | 2 | 8 | 5 | 3 | 5 | 8 | |
| 68 | 1 | | 3 | | 1 | 3 | | | 1 | 5 | 5 | 8 | 7 | 7 | 9 | 9 | 7 | 3 | 2 | 8 | 4 | 2 | 5 | 8 | |
| | | | | | | | | | 5 | 7 | 2 | 8 | 5 | 5 | 8 | 9 | 7 | | | | | | 1 | | |
| 69 | | | | | | | | | 1 | 3 | 1 | 6 | 3 | 4 | 8 | 8 | 4 | | | | | | | | |
| | | | | | | | | | 5 | | | | | | 4 | | | | | | | | | | |
| 70 | | | | | | | | | 1 | 3 | | 4 | 2 | 1 | 7 | 4 | 4 | | | | | | | | |
| | | | | | | | | | 5 | | | 1 | 1 | 1 | 7 | 1 | 3 | | | | | | | | |
| 71 | | | | | | | | | 1 | 4 | | 3 | | | 3 | 2 | | | | | | | | | |
| | | | | | | | | | 5 | 2 | | 1 | | | 1 | | | | | | | | | | |
| 72 | | | | | | 2 | | | 1 | 5 | | 4 | 3 | 4 | 8 | 6 | 6 | | | | | | 2 | | |
| | | | | | | | | | 5 | 2 | | 2 | 1 | 3 | 7 | 4 | 4 | | | | | | | | |
| 73 | 2 | | 3 | 4 | 3 | 8 | 9 | 2 | 1 | 5 | 4 | 7 | 5 | 7 | 9 | 9 | 7 | 3 | 2 | 9 | 7 | 7 | 9 | 9 | 4 |
| | | | | | | | | | 5 | 4 | 2 | 6 | 4 | 6 | 9 | 9 | 5 | 1 | 1 | 8 | 3 | 4 | 8 | 7 | |
| 74 | 1 | 1 | 1 | 2 | 2 | 5 | 3 | 1 | 1 | 5 | 3 | 6 | 4 | 6 | 9 | 9 | 7 | | 1 | 5 | | 1 | 8 | 5 | 1 |
| | | | | | | | | | 5 | 3 | 1 | 4 | 1 | 6 | 9 | 8 | 5 | | | | | 7 | 2 | | |
| 75 | 1 | | 1 | 1 | 3 | 6 | 5 | 2 | 1 | 5 | 2 | 6 | 4 | 6 | 9 | 9 | 6 | | 1 | 6 | | 1 | 7 | 7 | 3 |
| | | | | | | | | | 5 | 2 | | 3 | 1 | 5 | 9 | 8 | 5 | | | | | | 7 | 5 | |
| 76 | | | 1 | 1 | 2 | 3 | 2 | 2 | 1 | 5 | 3 | 6 | 3 | 5 | 9 | 8 | 6 | | 2 | 5 | | | 7 | 6 | 1 |
| | | | | | | | | | 5 | 2 | | 3 | 1 | 5 | 9 | 7 | 5 | | | | | | 5 | 4 | |
| 77 | | | | 2 | | 2 | 1 | | 1 | 4 | 2 | 6 | 3 | 4 | 8 | 8 | 3 | | | | | | 2 | 1 | |
| | | | | | | | | | 5 | 3 | 1 | 3 | 2 | 3 | 8 | 7 | 3 | | | | | | 1 | | |
| 78 | 5 | 2 | 6 | 4 | 6 | 7 | 9 | 4 | 1 | 7 | 5 | 9 | 7 | 8 | 9 | 9 | 8 | 3 | 2 | 9 | 8 | 7 | 9 | 9 | 7 |
| | | | | | | | | | 5 | 4 | 3 | 8 | 7 | 8 | 9 | 9 | 8 | 1 | | 6 | 6 | 5 | 9 | 9 | 7 |
| 79 | | | | 1 | 2 | 4 | | | 1 | 7 | 5 | 6 | 5 | 6 | 8 | 9 | 6 | | | | | | 2 | 1 | |
| | | | | | | | | | 5 | 2 | | 2 | 2 | 5 | 8 | 7 | 5 | | | | | | 1 | | |
| 80 | | | | | | | | | 1 | 4 | | 6 | 3 | 2 | 8 | 8 | 6 | | | | | | 1 | | |
| | | | | | | | | | 5 | 2 | | 3 | | 1 | 7 | 6 | 5 | | | | | | | | |
| 81 | | | | | | | | | 1 | 7 | 2 | 7 | 7 | 5 | 9 | 9 | 7 | | | | | | 3 | 3 | |
| | | | | | | | | | 5 | 4 | 1 | 5 | 3 | 4 | 9 | 9 | 6 | | | | | | 1 | 1 | |
| 82 | | | | | | 2 | | | 1 | 4 | | 4 | 5 | 4 | 8 | 7 | 5 | | | | | | | | |
| | | | | | | | | | 5 | 2 | | 2 | 2 | 4 | 8 | 6 | 5 | | | | | | | | |
| 83 | | | | | | 1 | | 1 | 1 | 6 | | 3 | 3 | 4 | 7 | 7 | 6 | | | | | | | | |
| | | | | | | | | | 5 | 1 | | | | 2 | 7 | 4 | 3 | | | | | | | | |
| 84 | | | | | | | | | 1 | 2 | 1 | 3 | 2 | 4 | 6 | 5 | 3 | | | | | | | | |
| | | | | | | | | | 5 | 1 | | | | 3 | 6 | 4 | 3 | | | | | | | | |
| 85 | 3 | 3 | 5 | 4 | 4 | 7 | 6 | 3 | 1 | 7 | 4 | 7 | 7 | 8 | 9 | 8 | 7 | 5 | 1 | 9 | 8 | 7 | 9 | 9 | 6 |
| | | | | | | | | | 5 | 5 | 3 | 6 | 6 | 7 | 8 | 8 | 6 | 2 | | 7 | 7 | 6 | 9 | 9 | |
| 86 | | | 3 | | 2 | 3 | 3 | 1 | 1 | 5 | 6 | 9 | 6 | 8 | 9 | 9 | 8 | | | 4 | 2 | | 6 | 6 | |
| | | | | | | | | | 5 | 3 | 2 | 6 | 4 | 7 | 9 | 9 | 6 | | | | | | 4 | 3 | |
| 87 | | | 5 | 2 | 1 | 1 | | | 1 | 6 | 3 | 8 | 4 | 5 | 9 | 8 | 5 | 2 | | 6 | | 2 | 4 | 7 | |
| | | | | | | | | | 5 | 5 | 2 | 8 | 4 | 5 | 9 | 8 | 4 | 1 | | 5 | | | 4 | 6 | |
| 88 | | | 1 | | | 1 | | | 1 | 4 | 2 | 5 | 4 | 5 | 9 | 9 | 5 | | | 3 | | | 3 | 5 | |
| | | | | | | | | | 5 | 3 | | 3 | 2 | 4 | 8 | 7 | 5 | | | 2 | | | 3 | 5 | |
| 89 | | | 3 | 1 | 1 | 1 | 4 | 2 | 1 | 5 | 2 | 7 | 4 | 4 | 8 | 8 | 4 | 1 | | 4 | | 2 | 5 | 4 | |
| | | | | | | | | | 5 | 4 | | 4 | 2 | 3 | 8 | 8 | 4 | | | 3 | | | 3 | 4 | |
| 90 | | | | | | | | | 1 | 3 | | | | 1 | 3 | 7 | 4 | | | | | | 2 | | |
| | | | | | | | | | 5 | 2 | | | | 2 | 7 | 5 | 3 | | | | | | | | |
| 91 | 1 | 1 | 3 | 3 | | | 3 | | 1 | 6 | 2 | 7 | 5 | 5 | 9 | 9 | 5 | 3 | | 7 | 4 | 2 | 4 | 8 | |
| | | | | | | | | | 5 | 3 | 1 | 6 | 4 | 5 | 9 | 9 | 4 | 2 | | 5 | 2 | 1 | 4 | 8 | |
| 92 | 2 | 2 | 3 | 3 | | 3 | 5 | 2 | 1 | 5 | 4 | 7 | 6 | 6 | 9 | 9 | 7 | 3 | 2 | 8 | 4 | 3 | 8 | 6 | 3 |
| | | | | | | | | | 5 | 5 | 2 | 6 | 6 | 5 | 9 | 9 | 7 | 1 | 2 | 6 | 3 | 2 | 7 | 5 | |
| 93 | | | | | | | | | 1 | 4 | 1 | 3 | 2 | 3 | 6 | 5 | 5 | | | 1 | | | 3 | | |
| | | | | | | | | | 5 | 3 | 1 | 3 | 2 | 3 | 6 | 5 | 5 | | | 1 | | | 2 | | |
| 94 | | | | | | 1 | 3 | | 1 | * | * | * | * | * | 8 | 9 | * | | | 2 | | | 4 | 3 | |
| | | | | | | | | | 5 | 4 | | 2 | 3 | 4 | 8 | 8 | 6 | | | 2 | | | 4 | | |
| 95 | | | | | | | | | 1 | 4 | | 6 | 2 | 4 | 9 | 6 | 4 | | | | | | 3 | | |
| | | | | | | | | | 5 | 1 | | 2 | | 3 | 8 | 5 | 4 | | | | | | | | |
| 96 | | | 2 | 1 | 2 | 4 | 1 | 1 | 1 | 4 | 5 | 7 | 4 | 7 | 9 | 9 | 6 | 2 | | 7 | 4 | 2 | 7 | 6 | |
| | | | | | | | | | 5 | 3 | 3 | 5 | 2 | 6 | 8 | 8 | 4 | | | 3 | | | 6 | 3 | |
| 97 | | | | | | | | | 1 | 3 | | 2 | | | 3 | | 2 | | | | | | | | |
| | | | | | | | | | 5 | 1 | | 1 | | | | | | | | | | | | | |
| 98 | | | | | | | | | 1 | 2 | | 4 | | | 4 | 7 | 6 | 4 | | | | | | | | |

TABLE 5-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| | | | | | | | | | 1 | | | | 2 | 3 | 6 | 5 | 4 | | | | | | | | |
| 99 | | | | | | | | | 5 | 6 | | 5 | 4 | 6 | 8 | 9 | 6 | | | | | | 3 | 6 | 3 |
| | | | | | | | | | 1 | 3 | | 2 | 2 | 5 | 7 | 8 | 5 | | | | | | 1 | 4 | |
| 100 | 1 | | | | 3 | 3 | | 1 | 5 | 7 | 3 | 7 | 6 | 6 | 9 | 9 | 7 | 2 | 1 | 3 | 1 | 1 | 6 | 7 | 1 |
| | | | | | | | | | 1 | 4 | 1 | 5 | 3 | 6 | 8 | 9 | 6 | | | 1 | | | 5 | 5 | |
| 101 | | | | | 1 | | | | 5 | 5 | | 6 | 4 | 5 | 8 | 8 | 6 | | | | | | 3 | 2 | |
| | | | | | | | | | 1 | 2 | | 1 | 2 | 4 | 8 | 6 | 5 | | | | | | 2 | 1 | |
| 102 | | | 1 | 2 | | | | 1 | 5 | 5 | 3 | 7 | 5 | 5 | 9 | 9 | 7 | | | 3 | | | 5 | 5 | 1 |
| | | | | | | | | | 1 | 3 | | 6 | 4 | 4 | 9 | 9 | 7 | | | 1 | | | 2 | 3 | 1 |
| 103 | | | | 2 | 2 | | | | 5 | 6 | 2 | 6 | 2 | 3 | 8 | 8 | 7 | | | | | | 2 | 1 | |
| | | | | | | | | | 1 | 3 | 2 | 2 | 1 | 2 | 7 | 6 | 6 | | | | | | 1 | | |
| 104 | | | | | | | | | 5 | 3 | 2 | 3 | 1 | 3 | 6 | 5 | 5 | | | | | | | | |
| | | | | | | | | | 1 | 1 | | 1 | | | 2 | 5 | 2 | 4 | | | | | | | |
| 105 | | | 4 | 3 | 2 | 5 | 8 | | 5 | 3 | | 6 | 3 | 5 | 8 | 9 | 6 | | | 2 | | 1 | 4 | 5 | 2 |
| | | | | | | | | | 1 | 1 | | 5 | 2 | 4 | 8 | 8 | 6 | | | | | | 3 | 3 | |
| 106 | 1 | | 2 | 3 | 1 | 3 | 2 | | 5 | 5 | 2 | 7 | 3 | 5 | 9 | 9 | 7 | | | 4 | 2 | | 5 | 5 | |
| | | | | | | | | | 1 | 3 | | 4 | 2 | 4 | 7 | 8 | 6 | | | 1 | | | 4 | 4 | |
| 107 | | | | 1 | 3 | 2 | 2 | | 5 | 2 | | 7 | 3 | 3 | 7 | 7 | 5 | | | 2 | | | 5 | 3 | |
| | | | | | | | | | 1 | 1 | | * | | | * | * | * | | | 1 | | | 4 | 2 | |
| 109 | | 2 | | | | 2 | 1 | | 5 | 4 | 2 | 6 | 3 | 3 | 8 | 8 | 5 | 2 | | 3 | | | 3 | 2 | |
| | | | | | | | | | 1 | 3 | 1 | 6 | 3 | 3 | 8 | 8 | 5 | 1 | | 2 | | | 2 | 1 | |
| 110 | 2 | | 2 | 3 | 2 | 4 | 5 | 1 | 5 | 6 | 6 | 8 | 8 | 8 | 9 | 9 | 7 | 3 | 3 | 9 | 7 | 4 | 9 | 8 | 3 |
| | | | | | | | | | 1 | 5 | 5 | 8 | 7 | 7 | 9 | 9 | 7 | 1 | 1 | 6 | 6 | 2 | 8 | 7 | 1 |
| 111 | | | | | 1 | 1 | 3 | | 5 | 4 | | 5 | 3 | 4 | 9 | 9 | 4 | | | 4 | | 1 | 4 | 2 | |
| | | | | | | | | | 1 | 2 | | 2 | 1 | 2 | 8 | 8 | 4 | | | 2 | | | 4 | 2 | |
| 112 | | | | | | | | | 5 | 3 | | 4 | 1 | 5 | 9 | 6 | 4 | | | | | | 2 | | |
| | | | | | | | | | 1 | 1 | | | | 3 | 7 | 4 | 4 | | | | | | | | |

By way of comparison, various structural isomers of the compounds of the present invention were prepared, in which the phenoxy and carboxamide moieties were located at different positions on the pyridine ring to the compounds of the present invention, which are all 2,6-isomers. The isomers were:

Compound A: N-(2,4-Difluorophenyl)-2-(3-trifluoromethylphenoxy)-3-pyridinecarboxamide. (DIFLUFENICAN)
Compound B: N-(2,4-Difluorophenyl)-2-(3-trifluoromethylphenoxy)-4-pyridinecarboxamide.
Compound C: N-(2,4-Difluorophenyl)-2-(3-trifluoromethylphenoxy)-5-pyridinecarboxamide.
Compound D: N-(2,4-Difluorophenyl)-3-(3-trifluoromethylphenoxy)-5-pyridinecarboxamide.
Compound E: N-(2,4-Difluorophenyl)-4-(3-trifluoromethylphenoxy)-2-pyridinecarboxamide.
Compound F: N-(2,4-Difluorophenyl)-3-(3-trifluoromethylphenoxy)-2-pyridinecarboxamide.
Compound G: N-(2,4-Difluorophenyl)-3-(3-trifluoromethylphenoxy)-4-pyridinecarboxamide.
Compound H: N-(2,4-Difluorophenyl)-3-(3-trifluoromethylphenoxy)-6-pyridinecarboxamide.

They were tested and the results were recorded in the same manner as for the compounds of the present invention. The results of tests on the following representative plant species

| | |
|---|---|
| soil drench tests: | maize, *Zea mays* (Mz) |
| | soya bean, *Glycine max* (S) |
| foliar spray tests: | maize, *Zea mays* (Mz) |
| | rice, *Oryza sativa* (R) |
| | barnyard grass, *Echinochloa crusgalli* (BG), |
| | oat, *Avena sativa* (O), |
| | mustard, *Sinapsis alba* (M) |
| | sugar beet, *Beta vulgaris* (SB) |
| | soya bean, *Glycine max* (S) |
| pre-emergence tests: | maize, *Zea mays* (Mz) |
| | barnyard grass, *Echinochloa crusgalli* (BG) | are set out in Table 6 below. The relevant activity data for the 2,6 isomer, the compound of Example 24, is also included in Table 6.

It will be observed from Table 6 that, as would be expected for a commercial compound, Compound A, diflufenican, shows good activity. However, all of the other isomers show negligible or limited activity. In contrast, and very surprisingly, the compound of the present invention shows substantial activity which in certain important respects exceeds that of the commercial compound.

TABLE 6

| Compound | Soil drench 10 kg/ha | | Dosage kg/ha | Foliar spray | | | | | | | Pre-emergence | |
|---|---|---|---|---|---|---|---|---|---|---|---|---|
| | Mz | S | | Mz | R | BG | O | M | SB | S | Mz | BG |
| A | 4 | 2 | 5 | 5 | 4 | 6 | 5 | 7 | 7 | 6 | 4 | 8 |
| | | | 1 | 3 | 3 | 4 | 3 | 7 | 7 | 6 | 3 | 8 |
| B | 0 | 0 | 5 | 0 | 0 | 0 | 0 | 2 | 0 | 0 | 0 | 0 |
| | | | 1 | 0 | 0 | 0 | 0 | 0 | 0 | 0 | 0 | 0 |
| C | 0 | 0 | 5 | 0 | 0 | 0 | 0 | 0 | 0 | 0 | 0 | 0 |
| | | | 1 | 0 | 0 | 0 | 0 | 0 | 0 | 0 | 0 | 0 |
| D | 0 | 0 | 5 | 0 | 0 | 0 | 0 | 4 | 2 | 0 | 0 | 0 |
| | | | 1 | 0 | 0 | 0 | 0 | 1 | 0 | 0 | 0 | 0 |
| E | 0 | 0 | 5 | 0 | 0 | 2 | 0 | 2 | 1 | 0 | 0 | 0 |

TABLE 6-continued

| Compound | Soil drench 10 kg/ha Mz | S | Dosage kg/ha | Foliar spray Mz | R | BG | O | M | SB | S | Pre-emergence Mz | BG |
|---|---|---|---|---|---|---|---|---|---|---|---|---|
|  |  |  | 1 | 0 | 0 | 0 | 0 | 1 | 0 | 0 | 0 | 0 |
| F | 0 | 0 | 5 | 0 | 0 | 0 | 0 | 3 | 0 | 0 | 0 | 0 |
|  |  |  | 1 | 0 | 0 | 0 | 0 | 3 | 0 | 0 | 0 | 0 |
| G | 0 | 0 | 5 | 0 | 0 | 1 | 1 | 7 | 2 | 3 | 0 | 0 |
|  |  |  | 1 | 0 | 0 | 0 | 0 | 6 | 2 | 2 | 0 | 0 |
| H | 0 | 0 | 5 | 0 | 0 | 0 | 0 | 0 | 0 | 0 | 0 | 0 |
|  |  |  | 1 | 0 | 0 | 0 | 0 | 0 | 0 | 0 | 0 | 0 |
| 24 | 4 | 2 | 5 | 5 | 4 | 7 | 5 | 7 | 9 | 6 | 4 | 8 |
|  |  |  | 1 | 4 | 3 | 7 | 4 | 7 | 9 | 6 | 3 | 8 |

We claim:
1. A compound of the formula I

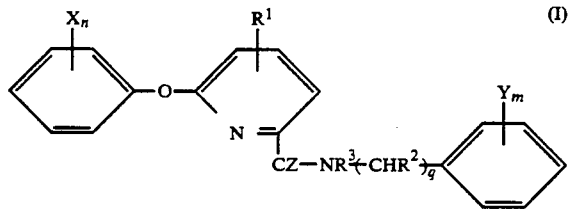

in which
Z represents an oxygen or sulphur atom;
$R^1$ represents a hydrogen or halogen atom or $C_{1-6}$ alkyl or halo ($C_{1-6}$) alkyl group;
$R^2$ represents a hydrogen atom or a $C_{1-6}$ alkyl group; q is 0 or 1;
$R^3$ represents a hydrogen atom or a $C_{1-6}$ alkyl or $C_{2-6}$ alkenyl group;
X independently represents a halogen atom or an optionally substituted $C_{1-6}$ alkyl or $C_{1-6}$ alkoxy group, or a $C_{2-6}$ alkenyloxy, $C_{2-6}$ alkynyloxy, cyano, carboxy, ($C_{1-6}$ alkoxy) carbonyl, ($C_{1-6}$ alkylthio) carbonyl, ($C_{1-6}$ alkyl) carbonyl, amido, ($C_{1-6}$ alkyl) amido, nitro, $C_{1-6}$ alkylthio, halo ($C_{1-6}$ alkyl) thio, $C_{2-6}$ alkenylthio, $C_{2-6}$ alkynylthio, $C_{1-6}$ alkylsulphinyl, $C_{1-6}$ alkylsulphonyl, ($C_{1-6}$ alkyl) oximino ($C_{1-6}$ alkyl) or ($C_{2-6}$ alkenyl) oximino ($C_{1-6}$ alkyl) group;
n is 0 or an integer from 1 to 5;
Y independently represents a halogen atom or a $C_{1-6}$ alkyl, nitro, cyano, halo ($C_{1-6}$) alkyl, $C_{1-6}$ alkoxy or halo ($C_{1-6}$) alkoxy group;
and m is 0 or an integer from 1 to 5,
said optional substituents being selected from halogen, phenyl, cyano, amino, hydroxy, $C_{1-6}$ alkoxy, and ($C_{1-6}$ alkyl) amino.
2. A compound of the formula I, as claimed in claim 1, wherein Z represents an oxygen atom.
3. A compound of the formula I, as claimed in claim 1, wherein $R^1$ represents a hydrogen atom.
4. A compound of the formula I, as claimed in claim 1, wherein q is 0, or q is 1 and $R^2$ represents a hydrogen atom or methyl group.
5. A compound of the formula I, as claimed in claim 1, wherein n is 0, or n is 1 or 2 and the or each group X independently represents a halogen atom, a $C_{1-4}$ alkoxy group, a $C_{1-4}$ alkyl group, a halo ($C_{1-4}$) alkyl group, a halo ($C_{1-4}$) alkoxy group, a nitro group, a $C_{2-4}$ alkenyloxy group, a $C_{1-4}$ alkylthio group, a $C_{1-4}$ alkylsulphonyl group, a ($C_{1-4}$ alkyl)oximino ($C_{1-4}$ alkyl) group, or a cyano group.
6. A compound of the formula I, as claimed in claim 1, wherein n is at least 1, and one substituent X is located at the 3-position, which X is a fluorine, chlorine or bromine atom or a trifluoromethyl, cyano, trifluoromethoxy or ethyl group.
7. A compound of the formula I, as claimed in claim 1, wherein m is 0; m is 1 and the group Y represents a halogen atom, or a cyano, methyl or trifluoromethyl group, or m is 2 or 3 and at least one Y is a halogen atom.
8. A compound of the formula I, as claimed in claim 1, wherein $R^3$ represents a hydrogen atom or a methyl, ethyl or allyl group.
9. A compound of the formula I, as claimed in claim 6, wherein $X_n$ represents a 3-trifluoromethyl or 3-cyano substituent; m is 0, or m is 1 or 2 and the or each Y is a fluorine atom; and $R^3$ represents a hydrogen atom or a methyl group.
10. A herbicidal composition which comprises a herbicidally effective amount of a compound as claimed in claim 1, together with at least one carrier.
11. A method of combating undesired plant growth at a locus, which comprises treating the locus with a herbicidally effective amount of a compound as claimed in claim 1.
12. A method of combating undesired plant growth at a locus, which comprises treating the locus with a herbicidally effective amount of a composition as claimed in claim 10.

* * * * *